(12) United States Patent
Atkinson et al.

(10) Patent No.: US 8,541,222 B2
(45) Date of Patent: *Sep. 24, 2013

(54) MODIFIED MICROORGANISMS WITH INACTIVATED LACTATE DEHYDROGENASE GENE

(75) Inventors: Anthony Atkinson, Surrey (GB); Roger Cripps, Surrey (GB); Ann Thompson, Auckland (NZ); Kirstin Eley, Surrey (GB); Mark Taylor, Surrey (GB); David Leak, Surrey (GB); Brian Rudd, Herts (GB); Simon Baker, Surrey (GB)

(73) Assignee: TMO Renewables Limited, Guildford, Surrey (GB)

( * ) Notice: Subject to any disclaimer, the term of this patent is extended or adjusted under 35 U.S.C. 154(b) by 828 days.

This patent is subject to a terminal disclaimer.

(21) Appl. No.: 11/915,930

(22) PCT Filed: Jun. 7, 2006

(86) PCT No.: PCT/GB2006/002087
§ 371 (c)(1),
(2), (4) Date: Sep. 29, 2008

(87) PCT Pub. No.: WO2006/131734
PCT Pub. Date: Dec. 14, 2006

(65) Prior Publication Data
US 2009/0197314 A1 Aug. 6, 2009

(30) Foreign Application Priority Data
Jun. 7, 2005 (GB) .................................. 0511602.5

(51) Int. Cl.
*C12N 1/20* (2006.01)
*C12N 15/63* (2006.01)
*C12N 15/85* (2006.01)
*A01N 63/00* (2006.01)

(52) U.S. Cl.
USPC .................. 435/252.31; 435/252.3; 435/455; 424/93.2

(58) Field of Classification Search
USPC ................. 424/93.2; 435/252.3, 252.31, 455
See application file for complete search history.

(56) References Cited

U.S. PATENT DOCUMENTS

| | | | |
|---|---|---|---|
| 5,238,833 A | | 8/1993 | Sanders et al. |
| 5,589,369 A | * | 12/1996 | Seidman et al. ................. 435/6 |
| 6,664,076 B2 | * | 12/2003 | Green et al. ................. 435/69.1 |
| 7,691,620 B2 | | 4/2010 | Green et al. |
| 8,021,865 B2 | | 9/2011 | Atkinson et al. |
| 8,143,038 B2 | | 3/2012 | Atkinson et al. |
| 2002/0034816 A1 | | 3/2002 | Green et al. |
| 2008/0305536 A1 | | 12/2008 | Atkinson et al. |
| 2010/0173373 A1 | | 7/2010 | Atkinson et al. |
| 2011/0217760 A1 | | 9/2011 | Atkinson et al. |
| 2011/0318802 A1 | | 12/2011 | Atkinson et al. |

FOREIGN PATENT DOCUMENTS

| | | |
|---|---|---|
| EP | 0124076 A2 | 11/1984 |
| EP | 0351717 A2 | 1/1990 |
| EP | 0 937 774 A1 | 8/1999 |
| GB | 2 074 188 A | 8/1981 |
| GB | 2171703 A | 9/1986 |
| JP | 2005-261239 A | 9/2005 |
| WO | WO 88/09379 A2 | 12/1988 |
| WO | WO 98/45425 A1 | 10/1998 |
| WO | WO 01/49865 A1 | 7/2001 |
| WO | WO 01/83784 A2 | 11/2001 |
| WO | WO 02/29030 A2 | 4/2002 |
| WO | WO 2006/117536 A1 | 11/2006 |
| WO | WO 2006/131734 A1 | 12/2006 |
| WO | WO 2007/039753 A1 | 4/2007 |
| WO | WO 2008/038019 A3 | 4/2008 |
| WO | WO 2009/022158 A1 | 2/2009 |
| WO | WO 2010/052499 A1 | 5/2010 |

OTHER PUBLICATIONS

Fortina et al., 2001, International Journal of Systematic and Evolutionary Microbiology, 51: 2063-2071.*

Desai, S G et al., "Cloning of L-lactate dehydrogenase and elimination of lactic acid production via gene knockout in *Thermoanaerobacterium saccharolyticum* JW/SL-YS485," Applied Microbiology and Biotechnology, Oct. 2004, pp. 600-605, vol. 65, No. 5, XP002393736.

Payton, M A, "Production of ethanol by thermophilic bacteria," Trends in Biotechnology, 1984, pp. 153-158, vol. 2, No. 6, Elsevier, Amsterdam, NL, XP000999007.

Biswas, I et al., "High-Efficiency Gene Inactivation and Replacement System for Gram-Positive Bacteria," Journal of Bacteriology, Jun. 1, 1993, pp. 3628-3635, vol. 175, No. 11, Washington, DC, US, XP000563688.

San Martin, R et al., "Pathways of ethanol production from sucrose by a mutant thermophilic *Bacillus* in continuous culture," Journal of General Microbiology, Jan. 5, 1993, pp. 1033-1040, vol. 139, Great Britain.

San Martin, R et al., "Development of a synthetic medium for continuous anaerobic growth and ethanol production with a lactate dehydrogenase mutant of *Bacillus stearothermophilus*," Journal of General Microbiology, Feb. 3, 1992, pp. 987-996, vol. 138, Great Britain.

"*Geobacillus*" retrieved from the NCBI Database via http://www.ncbi.nlm.nih.gov/Taxonomy/Browser/wwwtax.cgi?id=129337 on Mar. 22, 2012, 10 pages.

"*Geobacillus* Lactate Dehydrogenase in UniProtKB" retrieved from the UnitProt Database via http://www.uniprot.org/uniprot/?query=geobacillus++lactate+dehydrogenase&sort=score on Mar. 22, 2012, 2 pages.

"*Geobacillus* spo0A in UniProtKB" retrieved from the UnitProt Database via http://www.uniprot.org/uniprot/?query=geobacillus+spo0A&sort=score on Mar. 22, 2012, 3 pages.

Office Action dated Mar. 28, 2012 in U.S. Appl. No. 13/127,927, filed May 13, 2011.

(Continued)

*Primary Examiner* — Shin-Lin Chen
(74) *Attorney, Agent, or Firm* — Saliwanchik, Lloyd & Eisenschenk

(57) ABSTRACT

Modified microorganisms are prepared by inactivation of the endogenous lactate dehydrogenase gene. The microorganisms are deposited under NCIMB Accession Nos. 41277, 41278, 41279, 41280 or 41281.

6 Claims, 1 Drawing Sheet

(56) References Cited

OTHER PUBLICATIONS

U.S. Appl. No. 13/191,056, filed Jul. 26, 2011, Atkinson et al.
Barstow, D.A. et al. "Cloning, expression and complete nucleotide sequence of the *Bacillus stearothermophilus* L—lactate dehydrogenase gene" *Gene*, 1986, 46:47-55, abstract.
Breuer, M. et al. "High-throughput assay of (R)-phenylacetylcarbinol synthesized by pyruvate decarboxylase" *Anal Bioanal Chem*, 2002, 374:1069-1073.
Carlsson, J. et al. "Pyruvate Dehydrogenase Activity in *Streptococcus mutans*" *Infection and Immunity*, 1985, 49(3):674-678.
Database WPI Week 200567, Thomson Scientific, AN 2005-653380, XP002487167 & JP2005-261239A, Sep. 29, 2005.
De Graef, M.R. et al. "The Steady-State Internal Redox State (NADH/NAD) Reflects the External Redox State and Is Correlated with Catabolic Adaptation in *Escherichia coli*" *J. Bacteriol.*, Apr. 1999, 181(8):2351-2357.
Fong, J.C.N. et al. "Isolation and characterization of two novel ethanol-tolerant facultative-anaerobic thermophilic bacteria strains from waste compost" *Extremophiles*, 2006, 10:363-372.
Gao, H. et al. "The E1β and E2 Subunits of the *Bacillus subtilis* Pyruvate Dehydrogenase Complex Are Involved in Regulation of Sporulation" *Journal of Bacteriology*, May 2002, 184(10):2780-2788.
*Geobacillus thermoglucosidasius*. NCBI Databases, pp. 1-3, printed from the internet on Oct. 29, 2010.
Germain, P. et al. "Ethanol production by anaerobic thermophilic bacteria: regulation of lactate dehydrogenase activity in *Clostridium thermohydrosulfuricum*" *Appl Microbiol Biotechnol*, 1986, 24:300-305.
Hartley, B.S. et al. (May 1983) "Development and Economics of a Novel Thermophilic Ethanol Fermentation" Presentations from Biotech '83 London, May 4-6, 1983 First World Conference, Biotech, Northwood, Online Conf. Ltd, GB, pp. 895-905.
Hollmann, R. et al. "Pyruvate formation and suppression in recombinant *Bacillus megaterium* cultivation" *Journal of Biotechnology*, 2004, 111:89-96.
Jimenez, J. et al. "Selection of Ethanol-Tolerant Yeast Hybrids in pH-Regulated Continuous Culture" *Applied and Environmental Microbiology*, Apr. 1988, 54(4):917-922.
Kuisiene, N. et al. "Phylogenetic, Inter, and Intraspecific Sequence Analysis of spo0A Gene of the Genus *Geobacillus*" *Curr Microbiol*, 2009, 58:547-553.
Lapierre, L. et al. "D-Lactate Dehydrogenase Gene (*ldhD*) Inactivation and Resulting Metabolic Effects in the *Lactobacillus johnsonii* Strains La1 and N312" *Appl. Environ. Microbiol.*, Sep. 1999, 65(9):4002-4007.
Larsen, L. et al. "*Thermoanaerobacter mathranii* sp. Nov., an ethanol-producing, extremely thermophilic anaerobic bacterium from a hot spring in Iceland" *Arch Microbiol*, 1997, 168:114-119.
Lee, D.H. et al. "Ethanol Fermentation of Corn Starch by a Recombinant *Saccharomyces cerevisiae* Having Glucoamylase and α-Amylase Activities" *J. Food Sci. Nutr.*, 2001, 6(4):206-210.
Lessard, I.A.D. et al. "Expression in *Escherichia coli* of Genes Encoding the E1α and E1β Subunits of the Pyruvate Dehydrogenase Complex of *Bacillus stearothermophilis* and Assembly of a Functional E1 Component (α1β2) in Vitro" *The Journal of Biological Chemistry*, 1994, 269(14):10378-10383.
Lewis, R.J. et al. "Domain Swapping in the Sporulation Response Regulator Spo0A" *J. Mol. Biol.*, Mar. 31, 2000, 297(3):757-770.
Lynd, L.R. et al. "Thermophilic Ethanol Production: Investigation of Ethanol Yield and Tolerance in Continuous Culture" *Applied Biochemistry and Biotechnology*, 1991, 28/29:549-570.

Molle, V. et al. "The Spo0A regulon of *Bacillus subtilis*" *Molecular Microbiology*, 2003, 50(5):1683-1701.
Nakajima, R. et al. "Nucleotide Sequence of the *Bacillus stearothermophilus* α-Amylase Gene" *J. Bacteriol.*, Jul. 1985, 163(1):401-406.
Neveling, U. et al. "Gene and subunit organization of bacterial pyruvate dehydrogenase complexes" *Biochemica et Biophysica Acta*, 1998, 1385:367-372.
Nichols, N.N. et al. "Engineering lactic acid bacteria with pyruvate decarboxylase and alcohol dehydrogenase genes for ethanol production from *Zymomonas mobilis*" *J Ind Microbiol Biotechnol*, 2003, 30:315-321.
Niu, X.D. et al. "Cloning and nucleotide sequence of the gene for dihydrolipoamide acetyltransferase from *Saccharomyces cerevisiae*" *Proc. Natl. Acad. Sci. USA*, Oct. 1988, 85:7546-7550.
Rowe-Magnus, D.A. et al. "Identification of a Second Region of the Spo0A Response Regulator of *Bacillus subtilis* Required for Transcription Activation" *J. Bacteriol.*, Aug. 2000, 182(15):4352-4355.
Schütz, A. et al. "Crystal structure of thiamindiphosphate-dependent indolepyruvate decarboxylase from *Enterobacter cloacae*, an enzyme involved in the biosynthesis of the plant hormone indole-3-acetic acid" *Eur. J. Biochem.*, 2003, 270:2312-2321.
Schütz, A. et al. "Studies on structure-function relationships of indolepyruvate decarboxylase from *Enterobacter cloacae*, a key enzyme of the indole acetic acid pathway" *Eur. J. Biochem.*, 2003, 270:2322-2331.
Siegert, P. et al. "Exchanging the substrate specificities of pyruvate decarboxylase from *Zymomonas mobilis* and benzoylformate decarboxylase from *Pseudomonas putida*" *Protein Engineering, Design & Selection*, 2005, 18(7):345-357.
Stephenson, K. et al. "Molecular insights into the initiation of sporulation in Gram-positive bacteria: new technologies for an old phenomenon" *FEMS Microbiology Reviews*, 2005, 29:281-301.
Tomar, A. et al., "The effect of acetate pathway mutations on the production of pyruvate in *Escherichia coli*" *Appl Microbiol Biotechnol*, 2003, 62:76-82.
Wendisch, V.F. et al. "Metabolic engineering of *Escherichia coli* and *Corynebacterium glutamicum* for biotechnological production of organic acids and amino acids" *Current Opinion in Microbiology*, 2006, 9:268-274.
Witzmann, S. et al. "The pyruvate dehydrogenase complex from the thermophilic organisms: thermal stability and re-association from the enzyme components" *Biochemica et Biophysica Acta*, 1998, 13885:341-352.
Yomano, L.P. et al. "Isolation and characterization of ethanol-tolerant mutants of *Escherichia coli* KO11 for fuel ethanol production" *Journal of Industrial Microbiology & Biotechnology*, Feb. 1998, 20(2):132-138.
Office Action dated Nov. 17, 2009 in U.S. Appl. No. 11/913,480, filed Apr. 17, 2008.
Office Action dated Jun. 25, 2010 in U.S. Appl. No. 11/913,480, filed Apr. 17, 2008.
Office Action dated Feb. 18, 2011 in U.S. Appl. No. 12/066,526, filed Jun. 29, 2008.
Office Action dated Jun. 16, 2011 in U.S. Appl. No. 12/066,526, filed Jun. 29, 2008.
Office Action dated Mar. 7, 2011 in U.S. Appl. No. 12/376,826, filed May 22, 2009.
Office Action dated Sep. 15, 2011 in U.S. Appl. No. 13/127,927, filed May 13, 2011.
Office Action dated Sep. 23, 2011 in U.S. Appl. No. 12/376,826, filed May 22, 2009.
Office Action dated Oct. 14, 2011 in U.S. Appl. No. 13/191,056, filed Jul. 26, 2011.

* cited by examiner

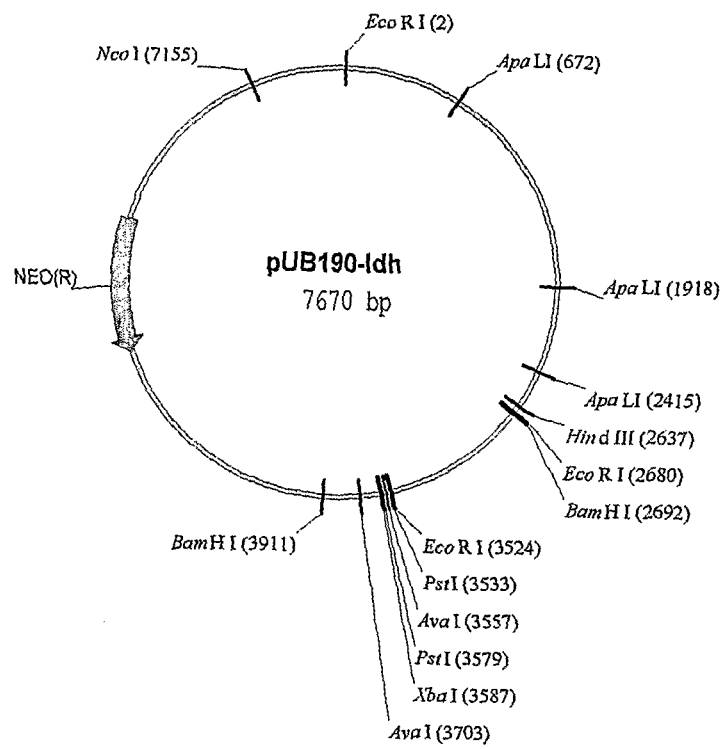
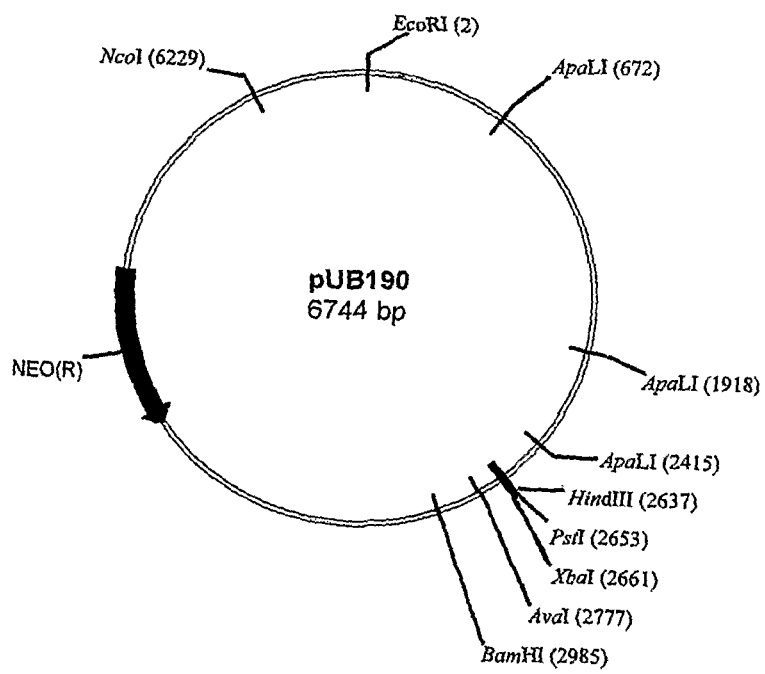

SEQUENCE LISTING

<160> NUMBER OF SEQ ID NOS: 6

<210> SEQ ID NO 1
<211> LENGTH: 6744
<212> TYPE: DNA
<213> ORGANISM: Geobacillus thermoglucosidasius

<400> SEQUENCE: 1

```
gaattcgtaa tcatggtcat agctgtttcc tgtgtgaaat tgttatccgc tcacaattcc      60
acacaacata cgagccggaa gcataaagtg taaagcctgg ggtgcctaat gagtgagcta     120
actcacatta attgcgttgc gctcactgcc cgctttccag tcgggaaacc tgtcgtgcca     180
gctgcattaa tgaatcggcc aacgcgcggg gagaggcggt ttgcgtattg ggcgctcttc     240
cgcttcctcg ctcactgact cgctgcgctc ggtcgttcgg ctgcggcgag cggtatcagc     300
tcactcaaag gcggtaatac ggttatccac agaatcaggg gataacgcag gaaagaacat     360
gtgagcaaaa ggccagcaaa aggccaggaa ccgtaaaaag gccgcgttgc tggcgttttt     420
ccataggctc cgcccccctg acgagcatca caaaaatcga cgctcaagtc agaggtggcg     480
aaacccgaca ggactataaa gataccaggc gtttccccct ggaagctccc tcgtgcgctc     540
tcctgttccg accctgccgc ttaccggata cctgtccgcc tttctccctt cgggaagcgt     600
ggcgctttct catagctcac gctgtaggta tctcagttcg gtgtaggtcg ttcgctccaa     660
gctgggctgt gtgcacgaac cccccgttca gcccgaccgc tgcgccttat ccggtaacta     720
tcgtcttgag tccaacccgg taagacacga cttatcgcca ctggcagcag ccactggtaa     780
caggattagc agagcgaggt atgtaggcgg tgctacagag ttcttgaagt ggtggcctaa     840
ctacggctac actagaagga cagtatttgg tatctgcgct ctgctgaagc cagttacctt     900
cggaaaaaga gttggtagct cttgatccgg caaacaaacc accgctggta gcggtggttt     960
ttttgtttgc aagcagcaga ttacgcgcag aaaaaaagga tctcaagaag atcctttgat    1020
cttttctacg gggtctgacg ctcagtggaa cgaaaactca cgttaaggga ttttggtcat    1080
gagattatca aaaaggatct tcacctagat ccttttaaat taaaaatgaa gttttaaatc    1140
aatctaaagt atatatgagt aaacttggtc tgacagttac caatgcttaa tcagtgaggc    1200
acctatctca gcgatctgtc tatttcgttc atccatagtt gcctgactcc ccgtcgtgta    1260
gataactacg atacgggagg gcttaccatc tggccccagt gctgcaatga taccgcgaga    1320
```

-continued

```
cccacgctca ccggctccag atttatcagc aataaaccag ccagccggaa gggccgagcg    1380
cagaagtggt cctgcaactt tatccgcctc catccagtct attaattgtt gccgggaagc    1440
tagagtaagt agttcgccag ttaatagttt gcgcaacgtt gttgccattg ctacaggcat    1500
cgtggtgtca cgctcgtcgt ttggtatggc ttcattcagc tccggttccc aacgatcaag    1560
gcgagttaca tgatccccca tgttgtgcaa aaaagcggtt agctccttcg gtcctccgat    1620
cgttgtcaga agtaagttgg ccgcagtgtt atcactcatg gttatggcag cactgcataa    1680
ttctcttact gtcatgccat ccgtaagatg cttttctgtg actggtgagt actcaaccaa    1740
gtcattctga aatagtgta tgcggcgacc gagttgctct gcccggcgt caatacggga     1800 taataccgcg ccacatagca gaactttaaa agtgctcatc attggaaaac gttcttcggg    1860
gcgaaaactc tcaaggatct taccgctgtt gagatccagt tcgatgtaac ccactcgtgc    1920
acccaactga tcttcagcat cttttacttt caccagcgtt tctgggtgag caaaaacagg    1980
aaggcaaaat gccgcaaaaa agggaataag ggcgacacgg aaatgttgaa tactcatact    2040 cttcctttt caatattatt gaagcattta tcagggttat tgtctcatga gcggatacat     2100
atttgaatgt atttagaaaa ataaacaaat aggggttccg cgcacatttc cccgaaaagt    2160
gccacctgac gtctaagaaa ccattattat catgacatta acctataaaa ataggcgtat    2220
cacgaggccc tttcgtctcg cgcgtttcgg tgatgacggt gaaaacctct gacacatgca    2280
gctcccggag acggtcacag cttgtctgta agcggatgcc gggagcagac aagcccgtca    2340
gggcgcgtca gcgggtgttg gcgggtgtcg ggctggctt aactatgcgg catcagagca    2400
gattgtactg agagtgcacc atatgcggtg tgaaataccg cacagatgcg taaggagaaa    2460
ataccgcatc aggcgccatt cgccattcag gctgcgcaac tgttgggaag ggcgatcggt    2520
gcgggcctct tcgctattac gccagctggc gaaagggga tgtgctgcaa ggcgattaag     2580
ttgggtaacg ccagggtttt cccagtcacg acgttgtaaa acgacggcca gtgccaagct    2640
tgcatgcctg caggtcgact ctagaaaatc aatctctttt tccaaagttt gttttttaaa    2700
tttagctgtc tcaatatgtt tacggtcaga gccacgttca ccacgcttca actcaaaacc    2760
ctgttttttc atatgctcgg ggaatttatc ttgtagccat aacagttctt gacgattaaa    2820
cacatttttt ccttgcagtt ttccatcacg cataggcaca acacctaaat gcatgtgagg    2880
ggtttgctca tcattatgaa ctgttgcata agcaatattt gcttgccat atcgttcgga     2940 aaataattta aactttcct caaaaaatcg ttttgttct cctggatcca gttgctcaaa      3000
aaaatcgcgg tcagatgtta ctagcaactc atttacaaga acagcatctt tcctcgtttt    3060
tcttgtacct gttttttgtg attcaataat ttctttgaca cgttcgttgt aatcaatatt    3120
tttatcattt ttcaaatcat aattttcacg tgttcgctca tggtcaatat catcattcgt    3180 tctactttt cgctctcttt gattatgaaa ttgcatgcct tttagtccag ctgatttcac    3240 ttttgcatt ctacaaactg cataactcat atgtaaatcg ctcctttta ggtggcacaa     3300 atgtgaggca ttttcgctct ttccggcaac cacttccaag taaagtataa cacactatac    3360
tttatattca taaagtgtgt gctctgcgag gctgtcggca gtgccgacca aaaccataaa    3420
acctttaaga cctttctttt ttttacgaga aaaagaaac aaaaaaacct gccctctgcc     3480
acctcagcaa aggggggttt tgctctcgtg ctcgtttaaa aatcagcaag ggacaggtag    3540
tattttttga gaagatcact caaaaaatct ccaccttta accttgcca atttttattt      3600 tgtccgtttt gtctagctta ccgaaagcca gactcagcaa gaataaaatt tttattgtct    3660
ttcggttttc tagtgtaacg gacaaaacca ctcaaaataa aaagataca agagaggtct    3720
```

```
ctcgtatctt ttattcagca atcgcgcccg attgctgaac agattaataa tagattttag    3780 cttttttattt gttgaaaaaa gctaatcaaa ttgttgtcgg gatcaattac tgcaaagtct    3840
cgttcatccc accactgatc ttttaatgat gtattggggt gcaaaatgcc caaaggctta    3900
atatgttgat ataattcatc aattccctct acttcaatgc ggcaactagc agtaccagca    3960
ataaacgact ccgcacctgt acaaaccggt gaatcattac tacgagagcg ccagccttca    4020
tcacttgcct cccatagatg aatccgaacc tcattacaca ttagaactgc gaatccatct    4080
tcatggtgaa ccaaagtgaa acctagttta tcgcaataaa aacctatact cttttttaata    4140 tccccgactg gcaatgccgg gatagactgt aacattctca cgcataaaat ccccttttcat    4200 tttctaatgt aaatctatta ccttattatt aattcaattc gctcataatt aatccttttt    4260
cttattacgc aaaatggccc gatttaagca cacccttttat tccgttaatg cgccatgaca    4320
gccatgataa ttactaatac taggagaagt taataaatac gtaaccaaca tgattaacaa    4380
ttattagagg tcatcgttca aaatggtatg cgttttgaca catccactat atatccgtgt    4440
cgttctgtcc actcctgaat cccattccag aaattctcta gcgattccag aagtttctca    4500
gagtcggaaa gttgaccaga cattacgaac tggcacagat ggtcataacc tgaaggaaga    4560
tctgattgct taactgcttc agttaagacc gaagcgctcg tcgtataaca gatgcgatga    4620
tgcagaccaa tcaacatggc acctgccatt gctacctgta cagtcaagga tggtagaaat    4680
gttgtcggtc cttgcacacg aatattacgc catttgcctg catattcaaa cagctcttct    4740
acgataaggg cacaaatcgc atcgtggaac gtttgggctt ctaccgattt agcagtttga    4800
tacactttct ctaagtatcc acctgaatca taaatcggca aaatagagaa aaattgacca    4860
tgtgtaagcg gccaatctga ttccacctga gatgcataat ctagtagaat ctcttcgcta    4920
tcaaaattca cttccacctt ccactcaccg gttgtccatt catggctgaa ctctgcttcc    4980
tctgttgaca tgacacacat catctcaata tccgaatagg gcccatcagt ctgacgacca    5040
agagagccat aaacaccaat agccttaaca tcatccccat atttatccaa tattcgttcc    5100
ttaatttcat gaacaatctt cattcttttct tctctagtca ttattattgg tccattcact    5160
attctcattc ccttttcaga taattttaga tttgcttttc taaataagaa tatttggaga    5220
gcaccgttct tattcagcta ttaataactc gtcttcctaa gcatccttca atccttttaa    5280
taacaattat agcatctaat cttcaacaaa ctggcccgtt tgttgaacta ctctttaata    5340
aaataatttt tccgttccca attccacatt gcaataatag aaaatccatc ttcatcggct    5400
ttttcgtcat catctgtatg aatcaaatcg ccttcttctg tgtcatcaag gtttaattt    5460 ttatgtattt cttttaacaa accaccatag gagattaacc ttttacggtg taaaccttcc    5520
tccaaatcag acaaacgttt caaattcttt tcttcatcat cggtcataaa atccgtatcc    5580
tttacaggat attttgcagt ttcgtcaatt gccgattgta tatccgattt atatttattt    5640
ttcggtcgaa tcatttgaac ttttacattt ggatcatagt ctaatttcat tgcctttttc    5700
caaaattgaa tccattgttt ttgattcacg tagttttctg tattcttaaa ataagttggt    5760
tccacacata ccaatacatg catgtgctga ttataagaat tatctttatt atttattgtc    5820
acttccgttg cacgcataaa accaacaaga ttttttattaa ttttttttata ttgcatcatt    5880 cggcgaaatc cttgagccat atctgacaaa ctcttattta attcttcgcc atcataaaca    5940
tttttaactg ttaatgtgag aaacaaccaa cgaactgttg cttttgtttt aataacttca    6000
gcaacaacct tttgtgactg aatgccatgt ttcattgctc tcctccagtt gcacattgga    6060
caaagcctgg atttacaaaa ccacactcga tacaactttc tttcgcctgt ttcacgattt    6120
```

-continued

```
tgtttatact ctaatatttc agcacaatct tttactcttt cagcctttt aaattcaaga      6180
atatgcagaa gttcaaagta atcaacatta gcgattttct tttctctcca tggtctcact      6240
tttccacttt ttgtcttgtc cactaaaacc cttgatttt catctgaata aatgctacta      6300
ttaggacaca taatattaaa agaaaccccc atctatttag ttatttgttt agtcacttat      6360
aactttaaca gatggggttt ttctgtgcaa ccaattttaa gggttttcaa tactttaaaa      6420
cacatacata ccaacacttc aacgcacctt tcagcaacta aaataaaaat gacgttattt      6480
ctatatgtat caagataaga aagaacaagt tcaaaaccat caaaaaaaga cacctttca      6540
ggtgctttt ttatttata aactcattcc ctgatctcga cttcgttctt tttttacctc      6600
tcggttatga gttagttcaa attcgttctt tttaggttct aaatcgtgtt tttcttggaa      6660
ttgtgctgtt ttatccttta ccttgtctac aaaccccta aaaacgtttt taaaggcttt      6720
taagccgtct gtacgttcct taag                                             6744
```

<210> SEQ ID NO 2
<211> LENGTH: 7673
<212> TYPE: DNA
<213> ORGANISM: Geobacillus thermoglucosidasius

<400> SEQUENCE: 2

```
gaattcgtaa tcatggtcat agctgtttcc tgtgtgaaat tgttatccgc tcacaattcc        60
acacaacata cgagccggaa gcataaagtg taaagcctgg ggtgcctaat gagtgagcta       120
actcacatta attgcgttgc gctcactgcc cgctttccag tcgggaaacc tgtcgtgcca       180
gctgcattaa tgaatcggcc aacgcgcggg gagaggcggt ttgcgtattg ggcgctcttc       240
cgcttcctcg ctcactgact cgctgcgctc ggtcgttcgg ctgcggcgag cggtatcagc       300
tcactcaaag gcggtaatac ggttatccac agaatcaggg gataacgcag gaaagaacat       360
gtgagcaaaa ggccagcaaa aggccaggaa ccgtaaaaag gccgcgttgc tggcgttttt       420
ccataggctc cgcccccctg acgagcatca caaaaatcga cgctcaagtc agaggtggcg       480
aaacccgaca ggactataaa gataccaggc gtttccccct ggaagctccc tcgtgcgctc       540
tcctgttccg accctgccgc ttaccggata cctgtccgcc tttctccctt cgggaagcgt       600
ggcgctttct catagctcac gctgtaggta tctcagttcg gtgtaggtcg ttcgctccaa       660
gctgggctgt gtgcacgaac cccccgttca gcccgaccgc tgcgccttat ccggtaacta       720
tcgtcttgag tccaacccgg taagacacga cttatcgcca ctggcagcag ccactggtaa       780
caggattagc agagcgaggt atgtaggcgg tgctacagag ttcttgaagt ggtggcctaa       840
ctacggctac actagaagga cagtatttgg tatctgcgct ctgctgaagc cagttacctt       900
cggaaaaaga gttggtagct cttgatccgg caaacaaacc accgctggta gcggtggttt       960
ttttgtttgc aagcagcaga ttacgcgcag aaaaaaagga tctcaagaag atcctttgat      1020
cttttctacg gggtctgacg ctcagtggaa cgaaaactca cgttaaggga ttttggtcat      1080
gagattatca aaaaggatct tcacctagat ccttttaaat taaaaatgaa gttttaaatc      1140
aatctaaagt atatatgagt aaacttggtc tgacagttac caatgcttaa tcagtgaggc      1200
acctatctca gcgatctgtc tatttcgttc atccatagtt gcctgactcc ccgtcgtgta      1260
gataactacg atacgggagg gcttaccatc tggccccagt gctgcaatga taccgcgaga      1320
cccacgctca ccggctccag atttatcagc aataaaccag ccagccggaa gggccgagcg      1380
cagaagtggt cctgcaactt tatccgcctc catccagtct attaattgtt gccgggaagc      1440
tagagtaagt agttcgccag ttaatagttt gcgcaacgtt gttgccattg ctacaggcat      1500
```

```
cgtggtgtca cgctcgtcgt ttggtatggc ttcattcagc tccggttccc aacgatcaag    1560
gcgagttaca tgatccccca tgttgtgcaa aaaagcggtt agctccttcg gtcctccgat    1620
cgttgtcaga agtaagttgg ccgcagtgtt atcactcatg gttatggcag cactgcataa    1680
ttctcttact gtcatgccat ccgtaagatg cttttctgtg actggtgagt actcaaccaa    1740
gtcattctga aatagtgta tgcggcgacc gagttgctct tgcccggcgt caatacggga    1800
taataccgcg ccacatagca gaactttaaa agtgctcatc attggaaaac gttcttcggg    1860
gcgaaaactc tcaaggatct taccgctgtt gagatccagt tcgatgtaac ccactcgtgc    1920
acccaactga tcttcagcat cttttacttt caccagcgtt tctgggtgag caaaaacagg    1980
aaggcaaaat gccgcaaaaa agggaataag ggcgacacgg aaatgttgaa tactcatact    2040 cttcctttt caatattatt gaagcattta tcagggttat tgtctcatga gcggatacat    2100
atttgaatgt atttagaaaa ataaacaaat aggggttccg cgcacatttc cccgaaaagt    2160
gccacctgac gtctaagaaa ccattattat catgacatta acctataaaa ataggcgtat    2220
cacgaggccc tttcgtctcg cgcgtttcgg tgatgacggt gaaaacctct gacacatgca    2280
gctcccggag acggtcacag cttgtctgta agcggatgcc gggagcagac aagcccgtca    2340
gggcgcgtca gcgggtgttg gcgggtgtcg ggctggctt aactatgcgg catcagagca    2400
gattgtactg agagtgcacc atatgcggtg tgaaataccg cacagatgcg taaggagaaa    2460
ataccgcatc aggcgccatt cgccattcag gctgcgcaac tgttgggaag ggcgatcggt    2520
gcgggcctct tcgctattac gccagctggc gaaaggggga tgtgctgcaa ggcgattaag    2580
ttgggtaacg ccagggtttt cccagtcacg acgttgtaaa acgacggcca gtgccaagct    2640
tggtaccgag ctcactagtc acggccgcca gtgtgctgga attcgccctt ggatcctttg    2700
cccttatgaa ccaaggaata gcagatgagt tagtattgat tgatgtaaat aagaataagg    2760
cagagggcga tgtgatggat ttaaatcacg gaaaagtatt cgcgccgaag ccgatgaata    2820
tttggtttgg agattatcaa gattgccaag acgccgattt ggtggtgatt tgtgcagggg    2880
ctaaccaaaa gccgggagaa acaagactgg atcttgttga caaaaatatt aatatcttca    2940
aaacgattgt cgattctgtg atgaaatccg gatttgatgg cgttttctt gtggcaacga    3000 acccagtgga tattttaacg tatgctactt ggaaatttag cgggttaccg aaagagcggg    3060
taatcggctc aggaacgatt cttgatacag caagattccg cttcttgcta agtgaatatt    3120
ttcaagtggc tccgaccaat gtacatgcgt atattattgg cgagcatggg atacagagc    3180 tgcctgtttg gagccatgcg gaaattggaa gcattccagt tgagcaaata ttgatgcaaa    3240
acgataacta tagaaaagag gatttagaca atatctttgt taatgttcgt gatgcggcat    3300
atcaaatcat tgagaaaaaa ggggcaacgt attacggcat tgcaatggga ttagtccgta    3360
tcactcgtgc tattttgcac aatgaaaatg ccatcttaac cgtttctgct catttggacg    3420
gccaatatgg cgaacgaaat gtttatattg gcgtgcctgc cattatcaac cgaaacggta    3480
ttcgtgaagt gatggaattg acgctaaatg aaacagaaca agggcgaatt ctgcagatat    3540
ccatcacact ggcggccgct cgagcatgca gcatgcctgc aggtcgactc tagaaaatca    3600
atctcttttt ccaaagtttg tttttttaaat ttagctgtct caatatgttt acggtcagag    3660
ccacgttcac cacgcttcaa ctcaaaaccc tgtttttca tatgctcggg gaatttatct    3720
tgtagccata acagttcttg acgattaaac acatttttc cttgcagttt tccatcacgc    3780
ataggcacaa cacctaaatg catgtgaggg gtttgctcat cattatgaac tgttgcataa    3840
gcaatatttt gcttgccata tcgttcggaa ataatttat aactttcctc aaaaaatcgt    3900
```

```
ttttgttctc ctggatccag ttgctcaaaa aaatctcggt cagatgttac tagcaactca    3960
tttacaagaa cagcatcttt cctcgttttt cttgtacctg ttttttgtga ttcaataatt    4020
tctttgacac gttcgttgta atcaatattt ttatcatttt tcaaatcata attttcacgt    4080
gttcgctcat ggtcaatatc atcattcgtt ctacttttc gctctctttg attatgaaat     4140
tgcatgcctt ttagtccagc tgatttcact ttttgcattc tacaaactgc ataactcata    4200
tgtaaatcgc tcctttttag gtggcacaaa tgtgaggcat tttcgctctt ccggcaacc     4260 acttccaagt aaagtataac acactatact ttatattcat aaagtgtgtg ctctgcgagg    4320
ctgtcggcag tgccgaccaa aaccataaaa cctttaagac cttctttttt tttacgagaa    4380 aaagaaaca aaaaaacctg ccctctgcca cctcagcaaa ggggggtttt gctctcgtgc     4440
tcgtttaaaa atcagcaagg acaggtagt attttttgag aagatcactc aaaaaatctc     4500
cacctttaaa cccttgccaa ttttttatttt gtccgttttg tctagcttac cgaaagccag   4560
actcagcaag aataaaattt ttattgtctt tcggttttct agtgtaacgg acaaaaccac    4620
tcaaaataaa aaagatacaa gagaggtctc tcgtatcttt tattcagcaa tcgcgcccga    4680
ttgctgaaca gattaataat agattttagc ttttttatttg ttgaaaaaag ctaatcaaat   4740
tgttgtcggg atcaattact gcaaagtctc gttcatccca ccactgatct tttaatgatg    4800
tattggggtg caaaatgccc aaaggcttaa tatgttgata taattcatca attccctcta    4860
cttcaatgcg gcaactagca gtaccagcaa taaacgactc cgcacctgta caaccggtg     4920 aatcattact acgagagcgc cagccttcat cacttgcctc ccatagatga atccgaacct    4980
cattacacat tagaactgcg aatccatctt catggtgaac caaagtgaaa cctagtttat    5040
cgcaataaaa acctactctc ttttaatat ccccgactgg caatgccggg atagactgta     5100
acattctcac gcataaaatc ccctttcatt ttctaatgta aatctattac cttattatta    5160
attcaattcg ctcataatta atccttttc ttattacgca aaatggcccg atttaagcac     5220
accctttatt ccgttaatgc gccatgacag ccatgataat tactaatact aggagaagtt    5280
aataaatacg taaccaacat gattaacaat tattagaggt catcgttcaa atggtatgc     5340 gttttgacac atccactata tatccgtgtc gttctgtcca ctcctgaatc ccattccaga    5400
aattctctag cgattccaga agtttctcag agtcggaaag ttgaccagac attacgaact    5460
ggcacagatg gtcataacct gaaggaagat ctgattgctt aactgcttca gttaagaccg    5520
aagcgctcgt cgtataacag atgcgatgat gcagaccaat caacatggca cctgccattg    5580
ctacctgtac agtcaaggat ggtagaaatg ttgtcggtcc ttgcacacga atattacgcc    5640
atttgcctgc atattcaaac agctcttcta cgataagggc acaaatcgca tcgtggaacg    5700
tttgggcttc taccgattta gcagtttgat acactttctc taagtatcca cctgaatcat    5760
aaatcggcaa aatagagaaa aattgaccat gtgtaagcgg ccaatctgat tccacctgag    5820
atgcataatc tagtagaatc tcttcgctat caaaattcac ttccaccttc cactcaccgg    5880
ttgtccattc atggctgaac tctgcttcct ctgttgacat gacacacatc atctcaatat    5940
ccgaataggg cccatcagtc tgacgaccaa gagagccata acaccaata gccttaacat      6000 catccccata tttatccaat attcgttcct taatttcatg aacaatcttc attctttctt    6060
ctctagtcat tattattggt ccattcacta ttctcattcc cttttcagat aattttagat    6120
ttgcttttct aaataagaat atttggagag caccgttctt attcagctat taataactcg    6180
tcttcctaag catccttcaa tcctttttaat aacaattata gcatctaatc ttcaacaaac   6240
tggcccgttt gttgaactac tctttaataa aataattttt ccgttcccaa ttccacattg    6300
```

-continued

```
caataataga aaatccatct tcatcggctt tttcgtcatc atctgtatga atcaaatcgc    6360
cttcttctgt gtcatcaagg tttaattttt tatgtatttc ttttaacaaa ccaccatagg    6420
agattaacct tttacggtgt aaaccttcct ccaaatcaga caaacgtttc aaattctttt    6480
cttcatcatc ggtcataaaa tccgtatcct ttacaggata ttttgcagtt tcgtcaattg    6540
ccgattgtat atccgattta tatttatttt tcggtcgaat catttgaact tttacatttg    6600
gatcatagtc taatttcatt gccttttttcc aaaattgaat ccattgtttt tgattcacgt    6660
agttttctgt attcttaaaa taagttggtt ccacacatac caatacatgc atgtgctgat    6720
tataagaatt atctttatta tttattgtca cttccgttgc acgcataaaa ccaacaagat    6780
ttttattaat tttttttatat tgcatcattc ggcgaaatcc ttgagccata tctgacaaac    6840
tcttatttaa ttcttcgcca tcataaacat tttaactgt taatgtgaga aacaaccaac    6900
gaactgttgg cttttgttta ataacttcag caacaacctt ttgtgactga atgccatgtt    6960
tcattgctct cctccagttg cacattggac aaagcctgga tttacaaaac cacactcgat    7020
acaactttct ttcgcctgtt tcacgatttt gtttatactc taatatttca gcacaatctt    7080
ttactctttc agccttttta aattcaagaa tatgcagaag ttcaaagtaa tcaacattag    7140
cgattttctt ttctctccat ggtctcactt ttccacttttt tgtcttgtcc actaaaaccc    7200
ttgatttttc atctgaataa atgctactat taggacacat aatattaaaa gaaaccccca    7260
tctatttagt tatttgttta gtcacttata actttaacag atggggtttt tctgtgcaac    7320
cattttaag ggttttcaat actttaaaac acatacatac caacacttca acgcaccttt    7380
cagcaactaa aataaaaatg acgttatttc tatatgtatc aagataagaa agaacaagtt    7440
caaaaccatc aaaaaagac accttttcag gtgcttttttt tatttataa actcattccc    7500
tgatctcgac ttcgttcttt ttttacctct cggttatgag ttagttcaaa ttcgttcttt    7560
ttaggttcta aatcgtgttt ttcttggaat tgtgctgttt tatcctttac cttgtctaca    7620
aaccccttaa aaacgttttt aaaggctttt aagccgtctg tacgttcctt aag           7673
```

<210> SEQ ID NO 3
<211> LENGTH: 29
<212> TYPE: DNA
<213> ORGANISM: Artificial
<220> FEATURE:
<223> OTHER INFORMATION: Oligonucleotide Primer

<400> SEQUENCE: 3
ggaattccct tatgaaccaa ggaatagca                                       29

<210> SEQ ID NO 4
<211> LENGTH: 31
<212> TYPE: DNA
<213> ORGANISM: Artificial
<220> FEATURE:
<223> OTHER INFORMATION: Oligonucleotide Primer

<400> SEQUENCE: 4
gcggccgcac ccgctctttc ggtaacccgc t                                    31

<210> SEQ ID NO 5
<211> LENGTH: 31
<212> TYPE: DNA
<213> ORGANISM: Artificial
<220> FEATURE:
<223> OTHER INFORMATION: Oligonucleotide Primer

```
<400> SEQUENCE: 5
gcggccgctt gctaagtgaa tattttcaag t                              31

<210> SEQ ID NO 6
<211> LENGTH: 28
<212> TYPE: DNA
<213> ORGANISM: Artificial
<220> FEATURE:
<223> OTHER INFORMATION: Oligonucleotide Primer

<400> SEQUENCE: 6
ctgcagcgtc aattccatca cttcacga                                  28
```

MODIFIED MICROORGANISMS WITH INACTIVATED LACTATE DEHYDROGENASE GENE

This application is a National Stage Application of International Application Number PCT/GB2006/002087, filed Jun. 7, 2006; which claims priority to Great Britain Application No. 0511602.5, filed Jun. 7, 2005.

FIELD OF THE INVENTION

This invention relates to the identification of microorganisms which may be adapted for the production of ethanol as a product of bacterial fermentation. In particular, the invention relates to ethanol production by thermophilic bacteria.

BACKGROUND TO THE INVENTION

Bacterial metabolism can occur through various different mechanisms depending on the bacterial species and environmental conditions. Heterotrophic bacteria, which include all pathogens, obtain energy from oxidation of organic compounds, with carbohydrates (particularly glucose), lipids and protein being the most commonly oxidised compounds. Biologic oxidation of these organic compounds by bacteria results in synthesis of ATP as the chemical energy source. The process also permits generation of more simple organic compounds (precursor molecules), which are required by the bacterial cell for biosynthetic reactions. The general process by which bacteria metabolise suitable substrates is glycolysis, which is a sequence of reactions that converts glucose into pyruvate with the generation of ATP. The fate of pyruvate in the generation of metabolic energy varies depending on the microorganism and the environmental conditions. There are three principle reactions of pyruvate.

First, under aerobic conditions, many micro-organisms will generate energy using the citric acid cycle and the conversion of pyruvate into acetyl coenzyme A, catalysed by pyruvate dehydrogenase (PDH).

Second, under anaerobic conditions, certain ethanologenic organisms can carry out alcoholic fermentation by the decarboxylation of pyruvate into acetaldehyde, catalysed by pyruvate decarboxylase (PDC) and the subsequent reduction of acetaldehyde into ethanol by NADH, catalysed by alcohol dehydrogenase (ADH).

A third process is the conversion of pyruvate into lactate which occurs through catalysis by lactate dehydrogenase (LDH).

There has been much interest in using micro-organisms for the production of ethanol using either micro-organisms that undergo anaerobic fermentation naturally or through the use of recombinant micro-organisms which incorporate the pyruvate decarboxylase and alcohol dehydrogenase genes. Although there has been some success in producing ethanol by using these micro-organisms, fermentation is often compromised by the increased concentration of the ethanol, especially where the micro-organism has a low level of ethanol tolerance.

Thermophilic bacteria have been proposed for ethanol production, and their use has the advantage that fermentation can be carried out at elevated temperatures which allows the ethanol produced to be removed as vapour at temperatures above 50° C.; this also permits fermentation to be carried out using high sugar concentrations. However, finding suitable thermophilic bacteria which can produce ethanol efficiently is problematic.

WO01/49865 discloses a Gram-positive bacterium which has been transformed with a heterologous gene encoding pyruvate decarboxylase and which has native alcohol dehydrogenase function, for the production of ethanol. The bacterium is a thermophilic *Bacillus* and the bacterium may be modified by the inactivation of the lactate dehydrogenase gene using transposon insertion. The bacteria disclosed in WO01/49865 are all derived from *Bacillus* Strain LLD-R, a sporulation deficient strain that arose spontaneously from culture, and in which the ldh gene has been inactivated by spontaneous mutation or by chemical mutagenesis. Strains LN and TN are disclosed as improved derivatives of strain LLD-R. However, all strains contain a Hae III type restriction systems that impedes plasmid transformation and therefore prevents the transformation within un-methylated DNA.

WO01/85966 discloses microorganisms that are prepared by in vivo methylation to overcome the restriction problems. This requires transformation with Hae III methyltransferase from *Haemophilus aegyptius* into strains LLD-R, LN and TN. However, strains LLD-R, LN and TN are unstable mutants and spontaneously revert to lactate-producing wild-type strains, particularly at low pH and in high sugar concentrations. This results in fermentation product changes from ethanol to lactate, making the strains unsuitable for ethanol production.

WO02/29030 discloses that strain LLD-R and its derivatives include a naturally-occurring insertion element (IE) in the coding region of the ldh gene. Transposition of this into (and out of) the ldh gene and subsequent gene inactivation is unstable, resulting in reversion. The proposed solution to this was to integrate plasmid DNA into the IE sequence.

Therefore, in the art, the production of microorganisms for ethanol production relies on modifying laboratory-produced chemically mutated *Bacillus* microorganisms, treating these with in vivo methylation procedures and further modifying the microorganisms to integrate plasmid DNA into the IE sequence. The procedure is complex, uncertain and there are also regulatory issues on how the strains can be used.

There is therefore a need for improved microorganisms for ethanol production.

SUMMARY OF THE INVENTION

According to a first aspect of the present invention, a thermophilic microorganism designated herein under any of NCIMB numbers 41277, 41278, 41279, 41280 and 41281 is modified to permit the increased production of ethanol, the modification being the inactivation of the lactate dehydrogenase gene of a wild-type thermophilic microorganism.

According to a second aspect of the present invention, a method for the production of ethanol comprises culturing a microorganism according to the definition provided above under suitable conditions in the presence of a C5 or C6 sugar.

According to a third aspect of the present invention, a method for the modification of a microorganism to increase the production of ethanol comprises obtaining a thermophilic microorganism defined as any of NCIMB Accession Nos. 41277, 41278, 41279, 41280 and 41281 and deleting the lactate dehydrogenase gene from the microorganism.

DESCRIPTION OF THE DRAWINGS

The present invention is described with reference to the accompanying drawing, wherein;

FIG. 1 is a graphic illustration of the plasmid maps for puB190 and puB190-ldh.

DESCRIPTION OF THE INVENTION

The present invention is based on the identification of wild-type microorganisms with desirable ethanol-producing properties and the modification of the wild-type thermophilic microorganism to disrupt the expression of the lactate dehydrogenase gene.

Inactivating the lactate dehydrogenase gene helps to prevent the breakdown of pyruvate into lactate, and therefore promotes (under appropriate conditions) the breakdown of pyruvate into ethanol using pyruvate decarboxylase and alcohol dehydrogenase, or equivalent enzymatic routes.

The wild-type microorganism of the invention may be any of the thermophilic microorganisms deposited under NCIMB number 41277, 41278, 41279, 41280 and 41281.

The microorganism selected for modification is said to be "wild-type", i.e. it is not a laboratory-produced mutant. The microorganism was isolated from environmental samples which contained thermophiles. The isolated wild-type microorganism was chosen due to its surprising ability to produce ethanol. However, unmodified, lactate is likely to be the major fermentation product. The isolate was also selected for the ability to grow on hexose and/or pentose sugars at thermophilic temperatures.

The microorganism of the invention has certain desirable characteristics which permit the microorganism to be used in a fermentation process. The microorganism has no restriction system, thereby avoiding the need for in vivo methylation. In addition, the microorganism is stable to at least 3% ethanol and has the ability to utilise C5 and C6 sugars as a substrate, including cellubiose and starch. The microorganism is also transformable at a high frequency. Furthermore, the microorganism has a growth rate in continuous culture of above 0.3 hours$^{-1}$.

The microorganism is a thermophile and grows in the temperature range of 40° C.-85° C. Preferably, the microorganism grows within the temperature range 50° C.-70° C. In addition, the microorganism grows in conditions of pH 6.5 or below, in particular pH6.5-pH4.5.

The nucleic acid sequence for lactate dehydrogenase is now known. Using this sequence, it is possible for the skilled person to target the lactate dehydrogenase gene to achieve inactivation of the gene through different mechanisms. It is preferred if the lactate dehydrogenase gene is inactivated either by the insertion of a transposon, or, preferably, by the deletion of the gene sequence or a portion of the gene sequence. Deletion is preferred, as this avoids the difficulty of reactivation of the gene sequence which is often experienced when transposon inactivation is used. In a preferred embodiment, the lactate dehydrogenase gene is inactivated by the integration of a temperature-sensitive plasmid (plasmid pUB190-ldh; deposited as NCIMB Accession No. 41276), which achieves natural homologous recombination or integration between the plasmid and the microorganism's chromosome. Chromosomal integrants can be selected for on the basis of their resistance to an antibacterial agent (kanamycin). The integration into the lactate dehydrogenase gene may occur by a single cross-over recombination event or by a double (or more) cross-over recombination event. A double cross-over event is preferred. The resulting mutant is stable without antibiotic selection.

Micro-organisms to be used in the invention have been deposited as NCIMB 41277, 41278, 41279, 41280 and 41281, NCIMB Ltd, Ferguson Building, Craibstone Estate, Bucksburn, Aberdeen, AB21 9YA, Scotland.

The microorganisms of the invention may be cultured under conventional culture conditions, depending on the thermophilic microorganism chosen. The choice of substrates, temperature, pH and other growth conditions can be selected based on known culture requirements, for example see WO01/49865 and WO01/85966.

The present invention will now be described, by way of example only, with reference to the accompanying drawings, in the following examples. The microorganism used to demonstrate the modifications to the ldh gene is *Geobacillus* 11955, although the methods disclosed herein are suitable for use with any of the microorganisms defined herein, as shown in Example 5.

Inactivation of the LDH Gene

Example 1

Single Crossover Mutation

Development of the LDH Knockout Vector

A partial ldh gene fragment of approx 800 bp was subcloned into the temperature-sensitive delivery vector pUB190 using HindIII and XbaI resulting in a 7.7 kb plasmid pUB190-ldh (FIG. 1 and SEQ ID NO.1). Ten putative *E. coli* JM109 (pUB190-ldh) transformants were verified by restriction analysis and two cultures used to produce plasmid DNA for transformation purposes. Digestion of pUB190-ldh with HindIII and XbaI releases the expected ldh fragment.

Transformation of *Geobacillus thermoglucosidasius* 11955 with pUB190-ldh

Transformants were obtained with all three plasmids tested after 24-48 hrs at 54° C. with kanamycin selection. The ldh transformants were purified from *Geobacillus thermoglucosidasius* (Gt) 11955 and verified by restriction analysis using HindIII and XbaI.

LDH Gene Knockout

Gene knockout was performed by integration of a temperature-sensitive plasmid into the ldh gene on the chromosome.

Plasmid pUB190-ldh replicates at 54° C. in Gt11955 but not at 65° C. Selection was maintained with kanamycin (kan) (12 μg/ml). The growth temperature was then increased to 65° C. (the plasmid is no longer replicative). Natural recombination or integration occurs between the plasmid and chromosome. Chromosomal integrants were selected for by their resistance to kanamycin. Integration was directed towards the ldh gene since an homologous sequence resides on the plasmid. Targeted integration into the ldh gene occurred by a process known as single cross-over recombination. The plasmid becomes incorporated into the ldh gene resulting in an inactive ldh gene. Tandem repeats may occur if several copies of the plasmid integrate.

Methodology and Results

Two different methods were attempted for integration:

Method 1: 4×50 ml TGP (kan) cultures were grown at 54° C. for 12-18 hours. The cells were pelleted by centrifugation and resuspended in 1 ml of TGP. The resuspension was plated (5×200 ml) on TGP (kan) plates and incubated overnight at 68° C. Integrants were picked and plated onto a 50-square grid on fresh TGP (kan) plates and incubated o/n at 68° C.

Method 2: 1×50 ml TGP (km) cultures was grown at 54° C. for 12-18 hours. 1 ml of the culture was used to inoculate 50 ml of fresh TGP (kan) cultures which was grown at 68° C. for 12-18 hours. This was sub-cultured the following day into 50 ml of fresh TGP (kan) cultures and grown at 68° C. for another 12-18 hours. The culture was plated out on TGP (km) plates and incubated at 68° C. overnight. Confluent growth was obtained on the plates. Single colonies were plated onto a 50-square grid on fresh TGP (kan) plates and incubated overnight at 68° C.

Screening

The putative integrants were screened for ldh gene knock-out using the following:

1) A Plate Screen

Replica plating of several hundred integrants onto SAM2 plates (with kan) at 68° C. Lactate negative cells produce less acid and may have a growth advantage over the wild type on fermentative media without buffers.

2) A PCR Screen

Colony PCR was used to determine whether the plasmid has integrated into the ldh gene. By choosing primers that flank the integration site, it was possible to determine whether ldh gene integration had occurred (no PCR fragment was amplified for inserts).

3) Lactate Assay

This assay determines whether the integrants produce lactate when grown overnight in SAM2 (kan) at 68° C. The culture supernatant was tested for the concentration of lactate with the Sigma lactate reagent for lactae determination. Lactate negative integrants were further characterised by PCR and evaluated in a fermenter for stability.

Electroporation Protocol for *Geobacillus thermoplucosidasius* NCIMB 11955

A frozen stock of NCIMB 11955 was made by growing an overnight culture in TGP medium (250 rpm at 55° C., 50 ml volume in a 250 ml conical flask, $OD_{600}$), adding an equal volume of 20% glycerol and dividing into 1 ml aliqouts and storing in cryotubes at −80° C. 1 ml of this stock was used to inoculate 50 ml of TGP in a 250 ml conical flask, incubated at 55° C., 250 rpm, until the culture reaches $OD_{600}$ 1.4.

The flask was cooled on ice for 10 minutes, then the culture centrifuged for 20 minutes at 4000 rpm at 4° C. The pellet was resuspended in 50 ml ice-cold electroporation medium and centrifuged at 4,000 rpm for 20 minutes. Three further washes were carried out, 1×25 ml and 2×10 ml, and then the pellet resuspended in 1.5 ml ice-cold electroporation medium and divided into 60 µl aliquots.

For the electroporation, 1-2 µl of DNA was added to 60 µl of electrocompetent cells in an eppendorf tube kept on ice, and gently mixed. This suspension was transferred to a pre-cooled electroporation cuvette (1 mm gap) and electroporated at 2500V, 10 µF capacitance and 600Ω resistance.

Immediately after the pulse, 1 ml TGP was added, mixed, and the suspension transferred to a screw top tube and incubated at 52° C. for 1 hour in a shaking waterbath. After incubation the suspension was either plated directly (e.g. 2×0.5 ml) or centrifuged at 4,000 rpm for 20 minutes, resuspended in 200 µl-500 µl TGP, and plated on TGP agar containing the appropriate antibiotic.

| Electroporation medium | TGP medium |
|---|---|
| 0.5M sorbitol | Tryptone 17 g/L |
| 0.5M mannitol | Soy peptone 3 g/L |
| 10% glycerol | $K_2HPO_4$ 2.5 g/L |
| | NaCl 5 g/L |
| | pH to 7.3 |
| | Additions post-autoclaving; |
| | Sodium pyruvate 4 g/l |
| | Glycerol 4 ml/L |

Inactivation of the LDH Gene.

Double Cross-Over Mutation

Primers were designed based on the available 11955 LDH sequence. The knock-out strategy was based on the generation of internal deletions within the LDH gene by two approaches.

In strategy 1, two existing unique restriction sites near the middle of the LDH coding sequence were exploited to generate a deletion. A single large per product was generated from genomic DNA covering most of the available LDH sequence, and cloned into the SmaI site in the multiple cloning site of pUC19. The pUC19 clone was then digested sequentially with BstEII and BsrGI and religated after Klenow digestion, to generate an internal deletion in the LDH gene between BstEII and BsrGI.

In strategy 2 (see Example 2) the LDH gene was cloned as 2 PCR products, introducing NotI sites on the oligonucleotide primers to allow the 2 PCR products to be ligated together in pUC19, with the generation of a deletion in the middle of the LDH sequence.

The two LDH genes with the internal deletions were subcloned into 3 potential delivery systems for *Geobacillus*.

| Plasmid | Details |
|---|---|
| pCU1 | 4.94 kb, shuttle vector based on pC194, carries cat & bla |
| pBT2 | 6.97 kb, shuttle vector derived from a ts mutant of pE194, carries cat and bla. |
| pTVOmcs | 4.392 kb, derived from pE194ts, carries cat (no Gram negative replicon). |

The delivery vectors were transformed into 11955 by electroporation.

Genetic Strategy Information: Development of Delivery Systems for Homologous Recombination.

To generate knockouts, an efficient system is required to deliver a mutated gene into the target organism and select for integration into the genome by homologous recombination with the target "wild-type" gene. In principle, this could be achieved by introducing the DNA on an *E. coli* vector without a Gram positive replicon but which carries a Gram negative selectable marker. This requires a high transformation efficiency. The electroporation method developed for *Geobacillus* 11955 generates $3\times10^4$ transformants per µg of DNA with pNW33N. The Gram positive replicon is derived from pBC1 in the BGSC catalogue, and from pTHT15 in the sequence database.

The cat gene on pNW33N is used for selection in both *E. coli* and *Geobacillus*. Temperature-sensitive mutants of pNW33N were generated by passaging the plasmid through the Statagene XL1 red mutator strain.

Example 2

Generation of an LDH Mutant by Gene Replacement

A further strategy was designed to generate a stable mutation of the LDH gene in *Geobacillus thermoglucosidasius* NCIMB 11955 by gene replacement. This strategy involved the generation of a 42 bp deletion close to the middle of the coding sequence, and the insertion at this position of 7 bp introducing a novel NotI restriction site. This inserted sequence was intended to cause a frame-shift mutation downstream.

The strategy involved generating the deletion using 2 PCR fragments using oligo primers introducing the novel NotI site. Primers were designed based on the partial sequence of the LDH coding region from 11955. The sequence of the primers used is shown below.

```
Fragment 1:
Primer 1 (forward);
(underlined sequence indicates bases introduced to
generate a novel EcoRI site1; SEQ ID NO. 3)
GGAATTCCCTTATGAACCAAGGAATAGCA
Primer 2 (reverse);
(underlined sequence indicates bases introduced to
generate a novel NotI site; SEQ ID NO. 4)
GCGGCCGCACCCGCTCTTTCGGTAACCCGCT.

Fragment 2:
Primer 3 (forward);
(underlined sequence indicates bases introduced to
generate a novel NotI site; SEQ ID NO. 5)
GCGGCCGCTTGCTAAGTGAATATTTTCAAGT.
Primer 4 (reverse);
(underlined sequence indicates bases introduced to
generate a novel PstI site; SEQ ID NO. 6)
CTGCAGCGTCAATTCCATCACTTCACGA.
```

Preparation of Genomic DNA.

Genomic DNA was prepared from 11955 to serve as template for PCR. Cells from a 20 ml overnight culture of 11955 grown in TGP medium at 52° C. were collected by centrifugation at 4,000 rpm for 20 mins. The cell pellet was resuspended in 5 ml of STE buffer 0.3M sucrose, 25 mM Tris HCl and 25 mM EDTA, adjusted to pH 8.0 containing 2.5 mg of lysozyme and 50 µl of 1 mg/ml ribonuclease A. This was incubated for 1 hour at 30° C., then 5 mg of proteinase K was added and 50 µl of 10% SDS followed by incubation at 37° C. for 1 hour. The lysed culture was then extracted sequentially with equal volumes of phenol/chloroform followed by chloroform before precipitation with isopropanol. After washing twice with ice-cold 70% ethanol, the DNA pellet was redissolved in 0.5 ml TE buffer.

Generation of LDH Deletion Construct.

PCR was carried out using a Robocycler Gradient 96 (Stratagene) and the reaction conditions were as follows: Cycle 1; denaturation at 95° C. for 5 min, annealing at 47° C. for 1 min, extension at 72° C. for 2 min, Cycle 2-30; denaturation at 95° C. for 1 min, annealing at 47° C. for 1 min, extension at 72° C. for 2 min, and a further incubation at 72° C. for 5 min. The enzymes used were an equal mixture of Pfu polymerase (Promega) and Taq polymerase (New England Biolabs, NEB). The buffer and dNTPs composition and concentration used was that recommended for Pfu by the suppliers. The PCR products obtained using genomic DNA from NCIMB 11955 as template were purified by agarose gel electrophoresis and eluted from the agarose gel by using the QIAquick Gel Extraction Kit (Qiagen). The purified PCR products were ligated to pUC19 (New England Biolabs) previously digested with SmaI and the ligation mixture was used to transform Escherichia coli DH10B (Invitrogen). Ampicillin resistant colonies were selected and the contained plasmids were isolated and characterised by restriction analysis, and the orientation of the inserts was established.

A plasmid (pTM002) with fragment 2 inserted into pUC19 (with the novel PstI site introduced on primer 4 closest to the PstI site in the multiple cloning site (mcs) of pUC19) was digested with NotI and PstI. The resulting fragment (approximately 0.4 kb) was ligated into a pUC19 plasmid (pTM001) bearing fragment 1 (with the novel EcoRI site introduced on oligo 1 closest to the EcoRI site in the mcs of pUC19) digested with NotI and PstI to linearise the plasmid. The ligation mixture was used to transform E. coli DH10B. Ampicillin-resistant colonies were selected and the contained plasmids were isolated and characterised by restriction analysis. A plasmid (pTM003) with the expected restriction pattern for the desired construct (the LDH coding region carrying the deletion and introduced NotI site) was identified and verified by sequencing using M13mp18 reverse and forward primers.

The mutated LDH gene was excised from pTM003 by digestion with HindIII and EcoRI and purified by agarose gel electrophoresis followed by elution from the agarose gel using the QIAquick Gel Extraction Kit (as an approximately 0.8 kb fragment). This fragment was treated with Klenow polymerase (NEB, according to manufacturers instructions) to generate blunt ends and introduced into the pUB190 vector. This was achieved by blunt-end ligation with pUB190 linearised by digestion with XbaI and then Klenow-treated followed by gel-purification as before. The ligation mixture was used to transform E. coli SCS110 (Stratagene). Ampicillin resistant colonies were selected and the contained plasmids were isolated and characterised by restriction analysis. A plasmid (pTM014) with the expected restriction pattern for the desired construct was identified and used to transform NCIMB 11955 by electroporation using the electroporation protocol as described in Example 1.

Generation and Characterization of a Gene-Replacement LDH Mutant by Double-Crossover.

A presumptive primary integrant of pTM014 obtained in this fashion (strain TM15) was used to obtain double recombinants (gene replacement). This was achieved by serial subculture of TM15 in TGP medium without kanamycin. Five successive shaken cultures were used, alternating between 8 hours at 54° C. and 16 hours at 52° C., using 5 ml TGP in 50 ml tubes (Falcon) at 250 rpm, 1% transfer at each stage. After these 5 passages, the resulting culture was serially diluted in TGP and 100 µl samples plated on TGP agar plates for incubation at 54° C. Replica-plating of the resultant colonies onto TGP agar containing 12 µg/ml kanamycin was used to identify kanamycin-sensitive colonies. After streaking to single colonies on agar to purify, these kanamycin sensitive derivatives were tested for lactate production, and as expected, proved a mixture of LDH$^+$ and LDH$^-$. One LDH$^-$ derivative, TM89, was further characterized by PCR and Southern blots.

Genomic DNA was prepared from TM15 (primary integrant) and TM89 (presumptive double recombinant LDH$^-$), and used as template for PCR using primers 1 and 4, using the conditions described above. Genomic DNA from 11955 was used as control. The PCR products (approx. 0.8 kb bands were obtained from all 3 templates) were purified by agarose gel electrophoresis and eluted from the agarose gel using the QIAquick Gel Extraction Kit. Samples were digested with NotI and run on a 0.7% agarose gel to visualize products. The PCR product of 11955 showed no evidence of NotI digestion, as expected, whereas the PCR product of TM89 gave 2 bands of around 0.4 kb, indicating the replacement of the wild-type gene with the mutated allele. NotI digestion of the PCR product of TM15, the primary integrant, gave predominantly the 2 bands seen with TM89, with a trace of the uncut (0.8 kb) band. This can be explained by the result obtained with Southern blotting of the TM15 genomic DNA.

Genomic DNA of 11955, TM15 and TM89 was digested with NotI, PstI and NotI, and HindIII and NotI, and subjected to agarose gel electrophoresis. The DNA was transferred onto a positively-charged nylon membrane (Roche) and hybridized with a DIG-labelled probe generated by PCR of the 11955 LDH gene using primers 1 and 4 with DIG-labeled dNTps, following the suppliers instructions (Roche Molecular Biochemicals DIG application manual). The hybridizing bands were visualized using the detection kit supplied (Roche). The Southern blot showed evidence of a much-amplified band of approx. 7.5 kb in the NotI digest of TM15, with similarly-amplified bands of approximately 7 and 0.4 kb in the HindIII/NotI and PstI/NotI digests of TM15, indicating integration of multiple tandem copies of pTM014 integrated at the LDH locus in this primary integrant. With all 3 restriction digests, TM89 showed evidence of a different restriction pattern showing an extra hybridizing band compared to 11955, consistent with gene replacement.

Example 3

Ethanol Production by the Wild-Type Thermophile

Reproducible growth and product formation was achieved in fed-batch and continuous cultures for the wild-type thermophile. Tables 1, 2 and 3 show the conditions used in the fermentation process.

TABLE 1

| Chemical | Vol./L | Final Conc. |
| --- | --- | --- |
| $NaH_2PO_4 \cdot 2H_2O$ | | 25 mM |
| $K_2SO_4$ | | 10 mM |
| Citric acid. $H_2O$ | | 2 mM |
| $Mg\ SO_4 \cdot 7H_2O$ | | 1.25 mM |
| $CaCl_2 \cdot 2H_2O$ | | 0.02 mM |
| Sulphate TE Solution | 5 ml | See below |
| $Na_2MoO_4 \cdot 2H_2O$ | | 1.65 µM |
| Yeast Extract | 10 g | |
| Antifoam | 0.5 ml | |
| Post-auto addns: | | |
| 4M Urea | 25 ml | 100 mM |
| 1% Biotin | 300 µl | 12 µM |
| 20% Glucose[2] | 50 ml | 1% |

TABLE 2

Sulphate Trace Elements Stock Solution

| Chemical | $gl^{-1}$ (ml) | $gl^{-1}$ (ml) | Medium Conc. |
| --- | --- | --- | --- |
| Conc. $H_2SO_4$ | 5 ml | 50 ml | |
| $Zn\ SO_4 \cdot 7H_2O$ | 1.44 | 14.4 | 25 µM |
| $Fe\ SO_4 \cdot 7H_2O$ | 5.56 | 55.6 | 100 µM |
| $Mn\ SO_4 \cdot H_2O$ | 1.69 | 16.9 | 50 µM |
| $Cu\ SO_4 \cdot 5H_2O$ | 0.25 | 2.5 | 5 µM |
| $Co\ SO_4 \cdot 7H_2O$ | 0.562 | 5.62 | 10 µM |
| $Ni\ SO_4 \cdot 6H_2O$ | 0.886 | 8.86 | 16.85 µM |
| $H_3BO_3$ | 0.08 | | |
| Del- $H_2O$ (final) | 1000 ml | 10 litres | |

TABLE 3

Fermenter Conditions

| Inoculum | 10% v/v |
| --- | --- |
| Volume | 1000 ml |
| Temperature | 60° C. |
| PH | 7.0 controlled with NaOH |
| Aeration | 0.4 vvm |
| $N_2$ flow | 0.05 lpm |
| Agitation | 400 rpm |
| Media | Urea Sulphates CDM for Fermenters |
| Sugar feed | 100 ml 50% glucose |

TABLE 4

Summary of improvements in growth of wild-type *Bacillus* in Batch Culture

| Media | Total Sugar added mM | OD600 | mM | | | | |
| --- | --- | --- | --- | --- | --- | --- | --- |
| | | | Pyruvate | Lactate | Formate | Acetate | Ethanol |
| Xylose | 603 | 8.5 | 9 | 187 | 5 | 75 | 22 |
| Glucose 1 | 504 | 4 | 2 | 295 | 36 | 28 | 39 |
| Glucose 2 | 504 | 3.7 | 19 | 322 | 111 | 55 | 123 |

Example 4

Increasing Ethanol Production by Thermophiles

In order to achieve the target ethanol yields and productivity from the thermophile, lactic acid production was minimised through the knock-out of L-Lactate Dehydrogenase (LDH) activity by inactivation of the ldh gene. There were two approaches taken to inactivate the ldh gene: a single crossover recombination of marker DNA into the ldh region of the chromosome, preventing its transcription, or a double recombination of homologous regions of DNA into the ldh gene to create a mutation within the gene region, rendering it non-functional.

The single cross-over approach rapidly generated LDH-negative mutants which showed an increase in ethanol production when compared to the wild-type strain.

Improvements in Ethanol Production by the LDH Mutants

The LDH-negative mutants were grown in fed-batch cultures, in the established minimal media to measure the increase in ethanol production resulting from the knock-out of LDH activity. The change in the metabolite profiles of the LDH mutants are shown in Table 5, compared to the optimum ethanol production from the wild-type strain. Table 6 shows the increase of ethanol production caused by the knock-out of LDH activity.

TABLE 5

Summary of increase in ethanol production achieved by lactate mutants

| Organism | Carbon Source | Total Sugar | OD600 | Pyruvate (mM) | Lactate (mM) | Formate (mM) | Acetate (mM) | Ethanol (mM) |
|---|---|---|---|---|---|---|---|---|
| w.t | gluc | 603 | 3.7 | 19 | 322 | 111 | 55 | 123 |
| ldh 35 | gluc | 336 | 4.7 | 82 | 22 | 128 | 37 | 220 |
| ldh 58 | gluc | 336 | 5.2 | 57 | 3 | 40 | 23 | 215 |

TABLE 6

Increased ethanol production by LDH mutants in fed-batch culture

| Organism | Carbon Source | OD600 | Glucose in feed g | Residual glu g | Lactate g | Lactate g/g cells | Lactate g/g glu | Ethanol g | Ethanol g/g cells | Ethanol g/g glu |
|---|---|---|---|---|---|---|---|---|---|---|
| w.t | gluc | 3.7 | 60.48 | 1.62 | 37.89 | 48.89 | 0.64 | 4.05 | 5.22 | 0.07 |
| ldh 35 | gluc | 4.7 | 60.48 | 17.80 | 1.98 | 1.36 | 0.05 | 10.12 | 6.95 | 0.24 |
| ldh 58 | gluc | 5.2 | 60.48 | 28.26 | 0.27 | 0.17 | 0.01 | 9.89 | 6.14 | 0.31 |

The LDH mutants produced significantly higher yields of ethanol than the wild-type thermophile, demonstrating the successful rerouting of the metabolism of these thermophiles. Further optimisation of culture conditions and media constituents for the LDH mutant strains will result in increased ethanol yields.

Example 5

Using the methods outlined in Example 2, the ldh modification was made to isolate NCIMB41277. The same transformation protocol was used, but transformation efficiency was optimised by incubation at 55° C. in recovery (as opposed to 52° C. in Example 2). The serial sub-culturing of the primary integrants was carried out in 2TY media to obtain double cross-overs with the ldh-negative phenotype. A stable knockout strain 41277KO4 was characterised in fed-batch and continuous fermentation. The results are shown in Table 7. This shows that the mutant 41227KO4 has significantly increased levels of ethanol production compared to the wild-type microorganism. The mutant is also stable in culture and does not revert back to the wild-type.

TABLE 7

Comparison between NCIMB 41277 and 41277KO4

| Strain | Sugar | $OD_{600}$ | Ethanol (mM) | Lactate (mM) | Formate (mM) | Acetate (mM) | Pyruvate (mM) |
|---|---|---|---|---|---|---|---|
| 41277 | Glucose | 1.8 | 1 | 42 | 0 | 29 | 2 |
| 41277 | Xylose | 1.1 | 0 | 36 | 0 | 34 | 3 |
| KO4 | Glucose | 2.6 | 71 | 0 | 85 | 40 | 4 |
| KO4 | Xylose | 2.3 | 50 | 0 | 71 | 21 | 2 |

The ethanol data for all wild-type isolates are shown in Table 8, demonstrating the ability of the isolates to produce ethanol in the wild-type form. This is unexpected as most wild-type microorganisms of this type will not produce ethanol.

TABLE 8

Ethanol data for isolates

| strain | Glucose | | | | Xylose | | | | Sucrose | | | |
| | | mM | | | | mM | | | | mM | | |
| | OD 600 | ethanol | lactate | acetate | OD 600 | ethanol | lactate | acetate | OD 600 | ethanol | lactate | acetate |
| --- | --- | --- | --- | --- | --- | --- | --- | --- | --- | --- | --- | --- |
| 11955 | 1.9 | 6 | 44 | 22 | 1.5 | 12 | 36 | 22 | 3.2 | 9 | 46 | 21 |
| 41277 | 1.8 | 1 | 42 | 29 | 1.1 | 0 | 36 | 34 | 3.1 | 0 | 39 | 25 |
| 41278 | 2.0 | 4 | 56 | 13 | 2.0 | 16 | 48 | 20 | 3.4 | 0 | 46 | 13 |
| 41280 | 1.6 | 2 | 34 | 32 | 1.2 | 6 | 37 | 28 | 3.3 | 7 | 34 | 22 |
| 41281 | 2.5 | 1 | 38 | 28 | 1.0 | 0 | 45 | 29 | 2.8 | 6 | 37 | 21 |

The invention claimed is:

1. A microorganism deposited under NCIMB number 41277, 41278, 41279, 41280, or 41281, wherein the microorganism has been modified to delete the endogenous lactate dehydrogenase gene.

2. The microorganism of claim 1, wherein the microorganism is deposited under NCIMB number 41277.

3. The microorganism of claim 1, wherein the microorganism is deposited under NCIMB number 41278.

4. The microorganism of claim 1, wherein the microorganism is deposited under NCIMB number 41279.

5. The microorganism of claim 1, wherein the microorganism is deposited under NCIMB number 41280.

6. The microorganism of claim 1, wherein the microorganism is deposited under NCIMB number 41281.

* * * * *

UNITED STATES PATENT AND TRADEMARK OFFICE
CERTIFICATE OF CORRECTION

PATENT NO.        : 8,541,222 B2                                          Page 1 of 1
APPLICATION NO.   : 11/915930
DATED             : September 24, 2013
INVENTOR(S)       : Atkinson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 855 days.

Signed and Sealed this
Fifteenth Day of September, 2015

Michelle K. Lee
*Director of the United States Patent and Trademark Office*